(12) United States Patent
Ko et al.

(10) Patent No.: US 12,025,548 B2
(45) Date of Patent: *Jul. 2, 2024

(54) APPARATUS FOR MEASURING PROPERTIES OF PARTICLES IN A SOLUTION AND RELATED METHODS

(71) Applicant: ORANGE BIOMED LTD., CO., Seoul (KR)

(72) Inventors: Ung Hyeon Ko, Seoul (KR); Seung Jin Kang, Seoul (KR); Eun Young Park, Seoul (KR)

(73) Assignee: ORANGE BIOMED LTD., CO., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/520,776

(22) Filed: Nov. 28, 2023

(65) Prior Publication Data

US 2024/0094188 A1    Mar. 21, 2024

Related U.S. Application Data

(63) Continuation of application No. 18/064,238, filed on Dec. 9, 2022, now Pat. No. 11,852,577, which is a
(Continued)

(30) Foreign Application Priority Data

Sep. 29, 2021  (KR) .................. 10-2021-0128520
Mar. 14, 2022  (KR) .................. 10-2022-0031378

(51) Int. Cl.
*G01N 15/1031* (2024.01)
*G01N 15/10* (2024.01)
(Continued)

(52) U.S. Cl.
CPC ..... *G01N 15/1031* (2013.01); *G01N 15/1023* (2024.01); *G01N 33/48707* (2013.01);
(Continued)

(58) Field of Classification Search
CPC ............... G01N 33/721; G01N 33/723; G01N 2015/012; G01N 2015/1027; G01N 2015/1029
See application file for complete search history.

(56) References Cited

U.S. PATENT DOCUMENTS 5,206,144 A    4/1993  Zeuthen et al.
5,642,734 A    7/1997  Ruben et al.
(Continued)

FOREIGN PATENT DOCUMENTS

EP    1162449 A1    12/2001
EP    2047909 A2 *  4/2009  .............. B01L 3/502
(Continued)

OTHER PUBLICATIONS

KR-20160014142-A—(Year: 2016).*
(Continued)

*Primary Examiner* — Kristina M Deherrera
*Assistant Examiner* — Fatemeh Esfandiari Nia
(74) *Attorney, Agent, or Firm* — Perkins Coie LLP

(57) ABSTRACT

The present technology relates to systems and associated methods for measuring properties of particles in a solution. In one or more embodiments, a particle measurement system is configured to generate a reference signal, communicate the reference signal across a plurality of resistors and overlapping pairs of electrodes that define detection regions for particulates traveling through a microchannel, and measure various properties of the particles based on detecting changes in the communicated reference signal.

24 Claims, 15 Drawing Sheets

Related U.S. Application Data continuation-in-part of application No. PCT/KR2022/019905, filed on Dec. 8, 2022, and a continuation-in-part of application No. PCT/KR2021/018280, filed on Dec. 3, 2021.

(51) Int. Cl.
- *G01N 33/487* (2006.01)
- *G01N 33/49* (2006.01)
- *G01N 15/01* (2024.01)

(52) U.S. Cl.
CPC ....... *G01N 33/49* (2013.01); *G01N 2015/012* (2024.01); *G01N 2015/1027* (2024.01); *G01N 2015/1029* (2024.01)

(56) References Cited

U.S. PATENT DOCUMENTS

| | | |
|---|---|---|
| 6,204,668 B1 | 3/2001 | Sequeira et al. |
| 6,399,293 B1 | 6/2002 | Pachl et al. |
| 6,949,070 B2 | 9/2005 | Ishler |
| 8,252,163 B2 | 8/2012 | Sugiyama et al. |
| 8,759,095 B2 * | 6/2014 | Vink ...................... A61P 29/00 |
| | | 435/325 |
| 8,789,405 B2 | 7/2014 | Sugiyama |
| 9,017,536 B2 | 4/2015 | Oishi et al. |
| 9,080,939 B2 | 7/2015 | Tsai et al. |
| 9,429,579 B2 | 8/2016 | Sugiyama et al. |
| 9,795,328 B2 | 10/2017 | Taub et al. |
| 9,977,037 B2 | 5/2018 | Yoshida et al. |
| 10,641,724 B2 | 5/2020 | Ainger et al. |
| 10,996,187 B2 | 5/2021 | Lee et al. |
| 11,009,479 B2 | 5/2021 | Liu et al. |
| 11,111,517 B2 | 9/2021 | Ichiyanagi et al. |
| 11,376,590 B2 | 7/2022 | Gurkan et al. |
| 11,385,244 B2 | 7/2022 | Shigemitsu et al. |
| 11,400,452 B2 | 8/2022 | Jagtiani |
| 11,747,348 B2 | 9/2023 | Ko et al. |
| 2005/0014249 A1 * | 1/2005 | Staimer ................ G01N 33/726 |
| | | 436/514 |
| 2006/0184037 A1 * | 8/2006 | Ince ....................... A61B 1/042 |
| | | 600/476 |
| 2006/0244964 A1 * | 11/2006 | Cox .................. G01N 15/1456 |
| | | 356/336 |
| 2010/0089774 A1 | 4/2010 | Manohar et al. |
| 2010/0145174 A1 | 6/2010 | Alferness et al. |
| 2010/0178660 A1 | 7/2010 | Adamczyk et al. |
| 2015/0268244 A1 | 9/2015 | Cho et al. |
| 2017/0227495 A1 * | 8/2017 | Gurkan ............ G01N 27/44791 |
| | | 204/601 |
| 2018/0235524 A1 | 8/2018 | Dunn et al. |
| 2018/0364186 A1 * | 12/2018 | Watkins ................ G01N 15/12 |
| 2019/0107533 A1 * | 4/2019 | Nagai ................ G01N 33/5094 |
| 2019/0232287 A1 | 8/2019 | Depa et al. |
| 2020/0101456 A1 | 4/2020 | Watkins et al. |
| 2020/0200734 A1 | 6/2020 | Yu et al. |
| 2021/0025904 A1 | 1/2021 | Snodgrass et al. |
| 2021/0072137 A1 | 3/2021 | Michel et al. |
| 2021/0229102 A1 | 7/2021 | Jagtiani |
| 2021/0239717 A1 | 8/2021 | Clarke et al. |
| 2021/0293693 A1 | 9/2021 | Bharadwaj et al. |
| 2022/0065876 A1 | 3/2022 | Connolly |
| 2022/0120768 A1 * | 4/2022 | Nishiyama ............. G01N 33/86 |
| 2022/0134339 A1 | 5/2022 | Hayashino et al. |
| 2022/0187184 A1 | 6/2022 | Al et al. |
| 2022/0362779 A1 | 11/2022 | Jagtiani |

FOREIGN PATENT DOCUMENTS

| | | | |
|---|---|---|---|
| EP | 2182345 | B1 | 6/2013 |
| EP | 2568281 | B1 | 11/2018 |
| EP | 2144057 | B1 | 4/2019 |
| EP | 2995947 | B1 | 1/2020 |
| JP | 2002538459 | A | 11/2002 |
| JP | H08292193 | A * | 10/2003 |
| JP | 2012529033 | A | 11/2012 |
| JP | 2017521679 | A | 8/2017 |
| KR | 20050120637 | A | 12/2005 |
| KR | 20070061042 | A | 6/2007 |
| KR | 20120111878 | A | 10/2012 |
| KR | 20130066841 | A | 6/2013 |
| KR | 20150108050 | A | 9/2015 |
| KR | 20150126476 | A | 11/2015 |
| KR | 101584083 | B1 | 1/2016 |
| KR | 101666847 | B1 | 10/2016 |
| KR | 20160014142 | A * | 10/2016 |
| KR | 101681170 | B1 | 12/2016 |
| KR | 101802289 | B1 | 12/2017 |
| KR | 101818368 | B1 | 1/2018 |
| KR | 101884314 | B1 | 8/2018 |
| KR | 101885964 | B1 | 8/2018 |
| KR | 101995253 | B1 | 7/2019 |
| KR | 102104654 | B1 | 4/2020 |
| KR | 20200097068 | A | 8/2020 |
| KR | 102174557 | B1 | 11/2020 |
| KR | 102281500 | B1 | 7/2021 |
| KR | 102315843 | B1 | 10/2021 |
| KR | 102403577 | B1 | 5/2022 |
| KR | 102439240 | B1 | 9/2022 |
| WO | 2010137470 | A1 | 12/2010 |
| WO | 2013153406 | A1 | 10/2013 |

OTHER PUBLICATIONS

JP-H08292193-A (Year: 2003).*
Makris, Konstantinos, and Loukia Spanou. "Is there a relationship between mean blood glucose and glycated hemoglobin?" Journal of diabetes science and technology 5.6 (2011): 1572-1583. (Year: 2011).*
EP-2047909-A2 (Year: 2009).*
International Search Report and Written Opinion mailed Mar. 17, 2023 for PCT Application No. PCT/KR2022/019905; 6 pages.
International Search Report mailed on Jul. 11, 2022 for International Patent Application No. PCT/KR2021/018280, 3 pages.
Tsai, et al., "Impedance measurement system for automatic determination of glycated hemoglobin", Rev. Sci. Instrum. 89, 065003, https://doi.org/10.1063/1.5025151, Jun. 28, 2018, 10 pages.

* cited by examiner

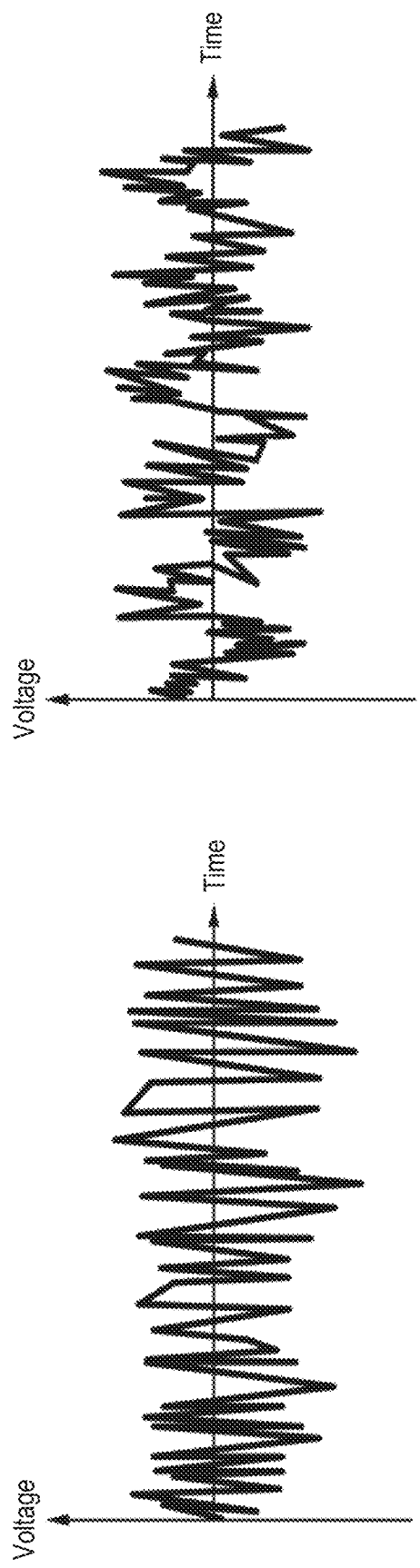
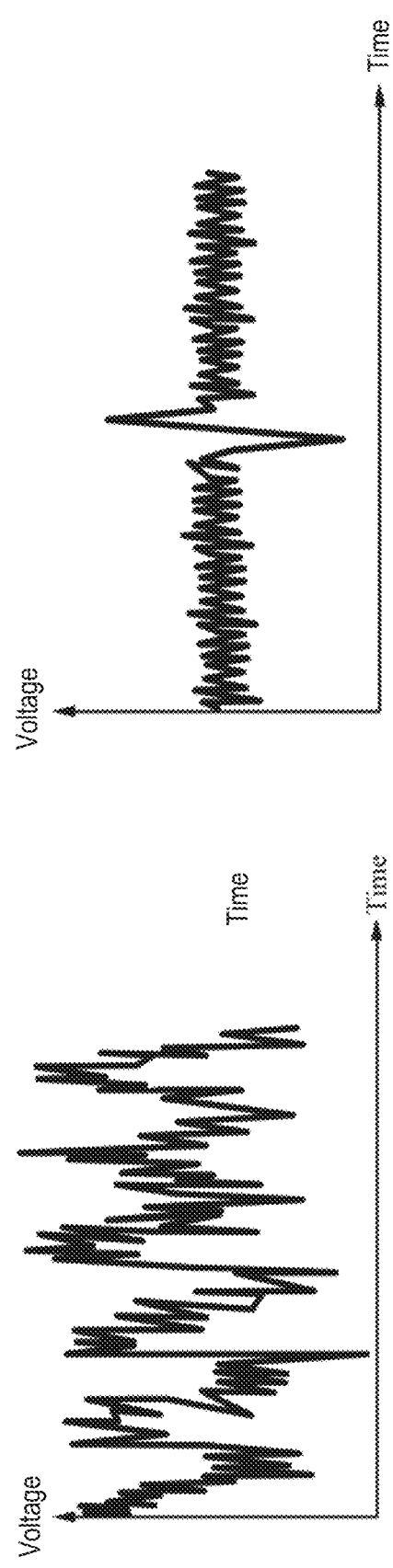
FIG. 6A
FIG. 6B
FIG. 6C
FIG. 6D

θ1 < θ2

$\theta 1 > \theta 2$ $\theta 1 = \theta 2$

APPARATUS FOR MEASURING PROPERTIES OF PARTICLES IN A SOLUTION AND RELATED METHODS

CROSS-REFERENCE TO RELATED APPLICATIONS

This application is a continuation of U.S. application Ser. No. 18/064,238, filed Dec. 9, 2022, which issued as U.S. Pat. No. 11,852,577 on Dec. 26, 2023, which is a continuation-in-part of International Application PCT/KR2022/019905, filed Dec. 8, 2022; which claims the benefit of Korean Patent Application No. 10-2022-0031378, filed Mar. 14, 2022. The 18/064,238 application is also a continuation-in-part of International Application PCT/KR2021/018280, filed Dec. 3, 2021, which claims the benefit of Korean Patent Application No. 10-2021-0128520, filed Sep. 29, 2021, issued as Korean Patent No. 10-2439474. All of these applications are hereby incorporated by reference for all purposes in their entireties.

TECHNICAL FIELD

This present disclosure relates to measuring properties of particles in a solution.

BACKGROUND

Various techniques for counting particles, such as cells, are being developed for analyzing different properties of solutions. For example, a light scattering method calculates the number and size of particles by directly transmitting light through the solution. The light scattering method focuses on determining the size or refractive index of the targeted particle and uses the correlation between the amount of light reflected by the particle surface and the particle size. However, when the surface of the particle is irregular, the degree of reflection of light varies with the surface contour, causing measurement errors.

A measurement method using electrical resistance sends a conductive solution between electrodes, via, e.g., a channel. An electric pulse is generated when a particle passes between the electrodes, and the measurement method uses the number of electric pulses to count the particles.

Typically, an impedance-based flow cytometer measures particle size and distribution by using the electrical resistance method. However, such flow cytometry requires a trained operator in a well-controlled microenvironment. Moreover, flow cytometry is difficult to implement outside of a laboratory environment due to the complexities of the required instruments. Therefore, it is necessary to devise a simpler structure for analysis or diagnosis, and for portability.

BRIEF DESCRIPTION OF THE DRAWINGS

Features, aspects, and advantages of the presently disclosed technology can be better understood with regard to the following drawings.

FIGS. 6A, 6B, 6C, and 6D are diagrams illustrating various states of an output signal being processed by the measurement unit according to some embodiments of the present technology.

Figure 1:
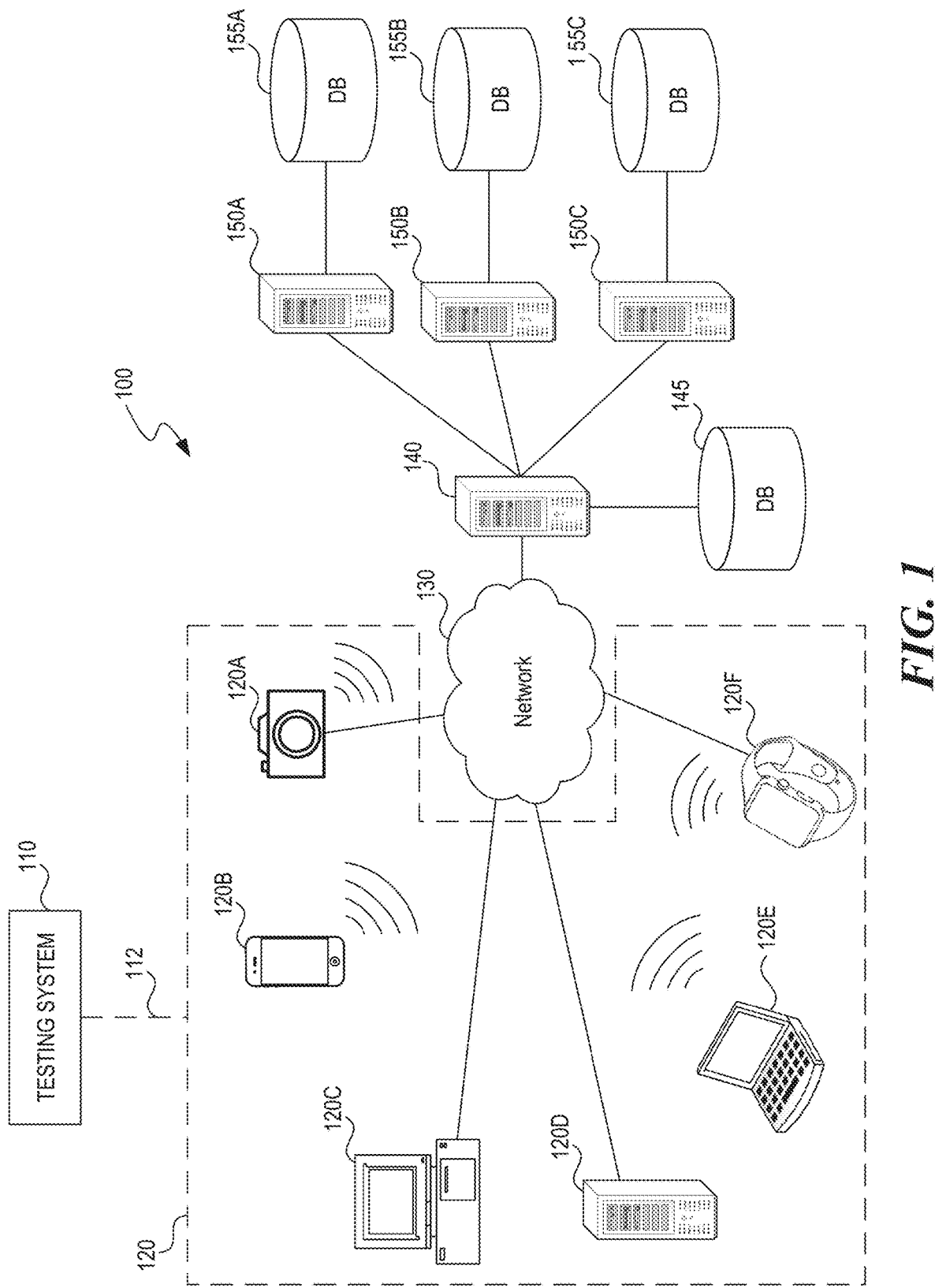
FIG. 1 is a block diagram illustrating an environment in which some embodiments of a particle measurement system for measuring properties of particles in a fluid can operate.

A person skilled in the relevant art will understand that the features shown in the drawings are for purposes of illustrations, and variations, including different and/or additional features and arrangements thereof, are possible.

DETAILED DESCRIPTION

The following disclosure describes systems, devices, and methods for measuring properties of particles in a fluid, including solutions. The present technology can include a particle measurement system or method for individually processing output signals and measuring properties of particles in a solution using a chip with a microchannel formed therein and a bridge-based circuit. The microchannel can be configured (via, e.g., a pump or capillary action) to convey and/or transfer particles (i.e., let particles slide through) such that measurements can be taken while the particles are moving in the microchannel. The microchannel can be configured (via, e.g., shape or size) to keep particles individually identifiable or distinguishable, such as by keeping particles spaced apart and letting only one particle pass through a point in the microchannel at a time. In some embodiments, the system or the method can detect the passage of fine particles using a sensor (e.g., a Wheatstone bridge) to detect changes in one or more signals traversing through one or more portions of the microchannel. The system or the method can measure one or more characteristics or traits (e.g., mechanical characteristics, deformability, stiffness, etc.) of particles using the magnitude and the duration of changes across an input signal and an output signal.

The particle measurement system can include a power unit that generates an input signal with a predetermined voltage, a chip on which a plurality of electrodes is sequentially arranged along a microchannel. The microchannel can be configured to pass a fluid that receives the processed input signal. The particle measurement system can further include a circuit unit (e.g., a portion of a bridge circuit) so as to achieve a predetermined electrical state with the plurality of electrodes on the chip. The particle measurement system can include a measurement unit for measuring and processing an output signal of the bridge circuit that differs from the processed input signal due to particles in the fluid passing through the microchannel.

The power unit can include a signal converting unit that converts the input signal (e.g., DC voltage) generated by the power unit into an AC (alternating current) or oscillating signal. The power unit can further amplify the converted AC signal and/or adjust the AC signal to a predetermined offset to generate a reference signal.

The measurement unit can detect a change (e.g., a phase change) in the reference signal as the particles are positioned between the electrodes on the chip. The measurement unit can use the detected change to count the particles in the fluid. Additionally or alternatively, the measurement unit can calculate the size of the particles in the fluid using the magnitude/amplitude and/or a duration of the change in the reference signal. The measurement unit can measure a change in the electrical state with the output signal measured by the bridge circuit after application of the offset-adjusted electrical signal.

The measurement unit can amplify the output signal using the offset-adjusted original electrical signal, convert the amplified output signal into an output signal by removing a specific frequency signal in the amplified output signal, and detect a phase signal associated with the change in the electrical state. The removed frequency can be set to be the same as or related to a frequency of the reference signal. The measurement unit can calculate a microchannel passage time of the particles using the wavelength of the DC output signal.

The particle measurement system can provide a voltage (e.g., the reference signal) to a sensor (e.g., a bridge circuit) that establishes a predetermined or a reference electrical state with a plurality of electrodes sequentially arranged on a microchannel. The reference electrical state can correspond to the reference signal traversing across the electrodes and through a fluid (e.g., electrolyte) passing through the microchannel. The particle measurement system can detect a change in an output signal generated the sensor due to particles in the fluid passing through the microchannel. For example, the particle measurement system can detect a phase change of the reference signal as the particles reach and pass through a location between the arranged electrodes. The particle measurement system can count the particles in the fluid by the number of times the phase changes. The method can also include calculating the size of the particles in the fluid using the magnitude/amplitude of the phase-changed output signal.

The particle measurement system can increase the accuracy in measuring various properties of particles suspended in solution using changes in the electrical signal. The increased accuracy can be achieved using the magnitude and time of the change of the electrical signal. The particle measurement system can efficiently measure characteristics of the particles even with a relatively low voltage through a simple circuit configuration. For healthcare applications, the particle measurement system can be used for clinical diagnosis by quantifying biological characteristics of measured particles using an individual reference value. Moreover, the particle measurement system can improve the consistency and robustness of the overall measurement while reducing the overall size in comparison to other conventional methods, thereby enabling the particle measurement system for home use.

For illustrative purposes, the present technology is described with respect to measuring one or more aspects related to red blood cells in a blood sample. However, it is understood that the present technology can be used to measure or analyze other fluid-suspended particulates and/or characteristics thereof.

Operating Environment

FIG. 1 is a block diagram illustrating an environment in which some embodiments of a particle measurement system 100 can operate. The particle measurement system 100 can include a testing system 110 that can measure or determine one or more properties associated with a fluid sample containing particulates therein. For example, the testing system 110 can determine various aspects, such as a number/concentration, a particle size (e.g., sizes of individual particles, average particle size, etc.), a rigidity of particles (e.g., rigidity of cell walls), analyte levels (e.g., a glycated hemoglobin level, glycated A1c hemoglobin level, etc.), a distribution associated with one or more properties, or the like, associated with particles (e.g., red blood cells) suspended within a blood sample. Additional details of the testing system 110 are described below.

The testing system 110 can communicate, via a direct wired or wireless communication link 112 or a network 130, with one or more client computing devices 120, examples of which can include an imaging device 120A, a smart phone or tablet 120B, a desktop computer 120C, a computer system 120D, a laptop computer 120E, and a wearable device 120F. These are only examples of some of the devices, and other embodiments can include other computing devices, such as other types of personal and/or mobile computing devices. In some embodiments, the computing devices 120 can collect various data from a user (e.g., analyte data from a wearable analyte monitor (for example, a continuous glucose monitor (CGM)), sleep data, heart rate data, blood pressure data, dietary information, exercise data, health metrics, etc.) and communicate the collected data to the testing system 110 and/or a service provider (e.g., a remote device/system, such as a server). The collected data can be leveraged for the testing/measuring processes. For example, the testing system 110 can include a processing system programmed to provide output based on correlates between real-time CGM data and glycated A1c hemoglobin levels. For example, the processing system can include a controller with one or more processors, memory storing programs analyzing the collected data executable to, for example, identify individual particles, over lapping particles, speed of travel of particles, flow rate of samples, etc. The client computing devices 120 can also communicate information, such as test results or other notifications, from the testing system 110 and/or the service provider to the user.

Accordingly, the computer devices 120 can operate in a networked environment using logical connections through the network 130 to the testing system 110 and/or one or more remote computers, such as a server computing device 140 or a cloud computing environment (e.g., devices 140, 145, 150, and/or 155). The networked environment can also be used to provide software updates to algorithms used in the testing system 110 and/or the one or more client computing devices 120. In some embodiments, the server 140 can be an edge server which receives client requests and coordinates fulfillment of those requests through other servers, such as servers 150A-C. Server computing devices 140 and 150 can include computing systems. Though each server computing device 140 and 150 is displayed logically as a single server, server computing devices can each be a distributed computing environment encompassing multiple computing devices located at the same or at geographically disparate physical locations. In some implementations, each server 150 corresponds to a group of servers.

The client computing devices 120 and the server computing devices 140 and 150 can each act as a server or client to other server/client devices. The server 140 can connect to a database 145. For example, the servers 150A-C can each connect to a corresponding database 155A-C. As discussed above, each server 150 can correspond to a group of servers, and each of these servers can share a database or can have their own database. Databases 145 and 155 can warehouse (e.g., store) information. For example, databases 145 and 155 can include a database of voltage patterns (e.g., waveform, sinusoidal, square, triangle, or similar envelop shapes of voltage levels measured over time) that correspond to certain types of particles (e.g., significantly deformed particles, white blood cells, diseased cells, overlapping cells). The particle measurement system 100 can match the detected voltage pattern to a voltage pattern in the database and either categorize it as unwanted noise and remove it, or record the type of particle as a data point. Though the databases 145 and 155 are displayed logically as single units, the databases 145 and 155 can each be a distributed computing environment encompassing multiple computing devices, can be located within their corresponding server, or can be located at the same or at geographically disparate physical locations.

The network 130 can be a local area network (LAN), a wide area network (WAN), and/or other wired, wireless, or combinational networks. Portions of the network 130 can include or communicate with the Internet or some other public or private network. The client computing devices 120 can be connected to the network 130 through a network interface, such as by wired or wireless communication. While the connections between the servers 140 and 150 are shown as separate connections, these connections can be any kind of local, wide area, wired, or wireless network, including the network 130 or a separate public or private network.

In some embodiments, the testing system 110 can communicate the analysis results to the server 140 corresponding to other entities, such as a healthcare provider, a further health tracking or comprehensive health analysis service, or the like. Alternatively, the testing system 110 can provide the measurements to the server 140 (e.g., without local analysis at the testing system 110), and the remote service provider can analyze the provided measurements.

Testing Configuration

Figure 2:
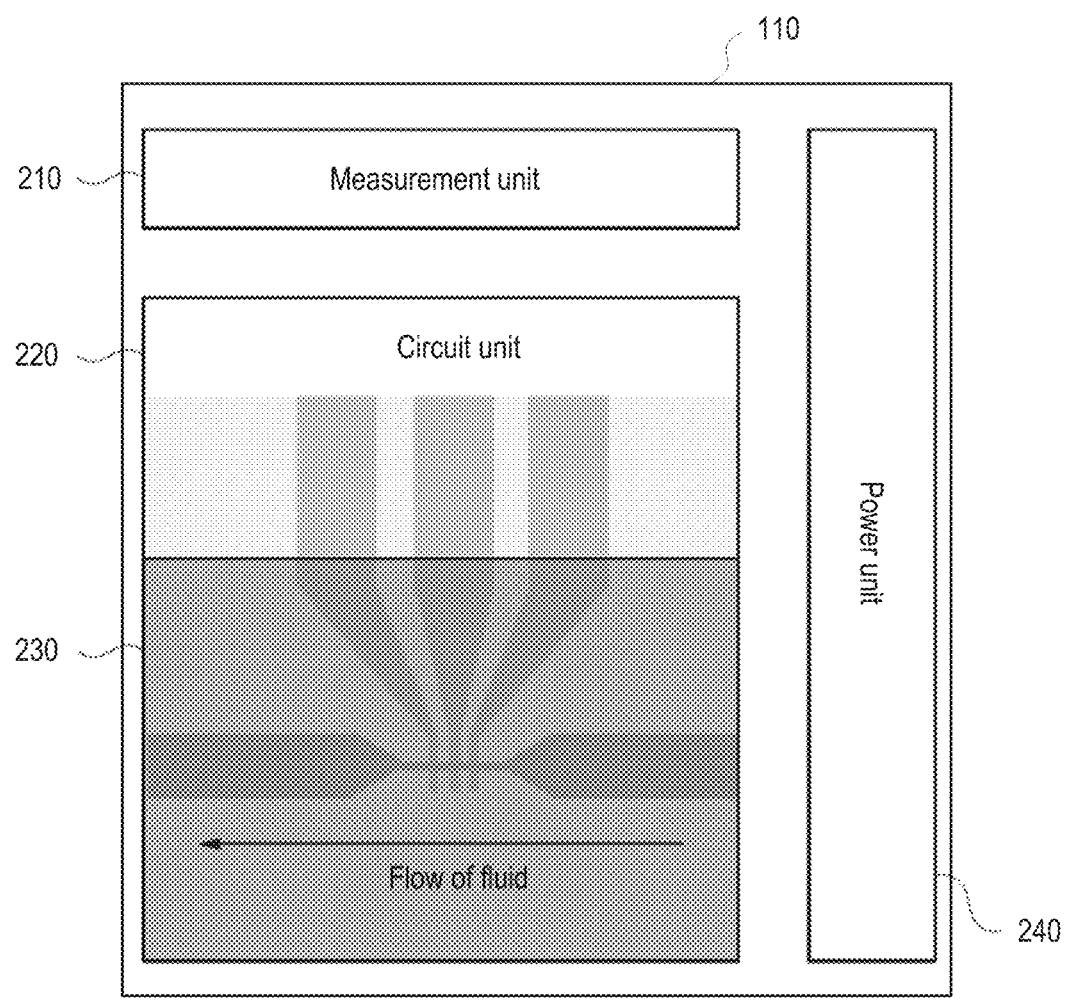
FIG. 2 is a block diagram illustrating the testing system according to some embodiments of the present technology.

FIG. 2 is a block diagram illustrating the testing system 110 for measuring properties of particles in a fluid according to some embodiments of the present technology. The testing system 110 can include a control apparatus and a fluid sample chip 230. The fluid sample chip 230 can receive the fluid and the particles suspended therein and can couple to the control apparatus. When coupled, the control apparatus can include circuits or components configured to (1) manipulate the fluid and the particles and (2) gather one or more types of measurements during the manipulation. In some embodiments, the control apparatus can include (1) a power unit 240 configured to generate and process an input signal, (2) a circuit unit 220 having circuitry configured to generate an output signal representative of one or more properties of the manipulated fluid/particulates, and a measurement unit 210 that receives and processes the output signal from the circuit unit 220. The control apparatus can further include a pump configured to facilitate the manipulation of the fluid/particulate.

The fluid sample chip 230 may be integrated with the testing system 110 or be a separate, detachable, and couplable component. Accordingly, a user may select and utilize chips that are configured to measure specific particles in a solution.

In some embodiments, the fluid sample chip 230 can include an inlet, an outlet, and a microchannel extending between the inlet and outlet on a substrate. The inlet can be configured to receive the fluid with the suspended particulates, and the outlet can be configured to receive the fluid and the particulates that have traversed through the microchannel. The microchannel can have a shape and/or a dimension that is associated with the targeted fluid and particulate. For example, the microchannel can have a width and/or a height that is less than a corresponding average dimension of a red blood cell by a predetermined amount (e.g., 5%-25% less than a diameter or a thickness, respectively). The inlet and the outlet can be configured to couple to the pump, thereby applying an external force that compresses and pushes the red blood cells through the microchannel.

The fluid sample chip 230 can include electrodes configured to electrically couple to the circuit unit 220 and form a sensor circuit (e.g., a bridge circuit) together with components therein. The power unit 240 can send an input or a reference signal to the electrodes on the fluid sample chip 230. In some embodiments, the inlet and/or the microchannel can include an electrolyte that can electrically conduct the input signal. Accordingly, the provided signal can be communicated through a pair of electrodes by traversing across a detection region that is on the microchannel and between the pair of electrodes. The electrolyte and/or the fluid can establish an initial or a reference state for the communicated signal. When the particulate traversing through the microchannel reaches and passes the detection region, the particulate can alter one or more electrical properties in the connection between the electrodes. The altered electrical properties can cause a change in the communicated signal (e.g., a corresponding voltage pattern such as an observation voltage levels at a designated node over time), thereby deviating away from the initial/reference state. Accordingly, the measurement unit 210 may detect the changes in the electrical characteristics of the signal traversing across the detection region, and the detected changes can be used to measure various properties the particles.

The measurement unit 210 can measure an output signal from the sensor circuit and compare the output signal to the reference state. The output signal can include a non-periodic or periodic voltage pattern (e.g., waveform, sinusoidal, square, triangle, or similar envelop shapes of voltage levels measured over time). The measurement unit 210 can detect the particles via a change in the output signal.

For example, as the particles in the solution reach detection regions between pairs of electrodes, the measurement unit 210 can detect a change in the communicated signal. For example, a phase, amplitude, and/or wavelength change can be detected based on one or more peak levels of the output signal. The microchannel can be configured (via, e.g., a shape and/or a size) to keep particles individually identifiable or distinguishable. For example, the microchannel can be configured to keep particles spaced apart and let only one particle pass through a point in the microchannel at a time, such that the measurement unit 210 may count the detected phase changes to count particles in a fluid as the particles successively pass through the microchannel. The microchannel can also be configured (via, e.g., a shape and/or a size) to prevent rotation and maintain the orientation of the particle while the particle slides through. If there is an unwanted overlap of particles such that two or more particles pass through a point in the microchannel at the same time, the measurement unit 210 can detect such overlap (e.g., based on a voltage pattern in a database) and omit corresponding signals. The solution containing the particles can also be diluted to lower the probability of such overlap. At this time, the testing system 110 can convert an input signal or power from the power unit 240, which may include or couple to a power source, such as a portable DC power supply (e.g., electrical battery) into an AC signal.

Figure 3:
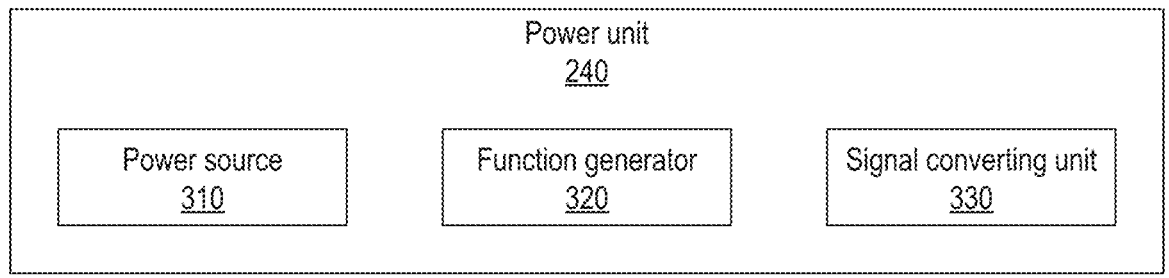
FIG. 3 is a block diagram illustrating a power unit of the testing system according to some embodiments of the present technology.
Figure 4A:
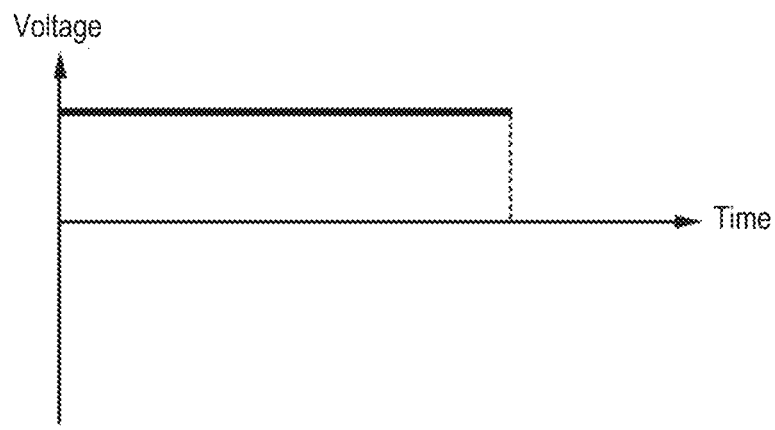
FIGS. 4A, 4B, and 4C are diagrams illustrating various stages of an input signal being processed by the power unit according to some embodiments of the present technology.
Figure 4B:
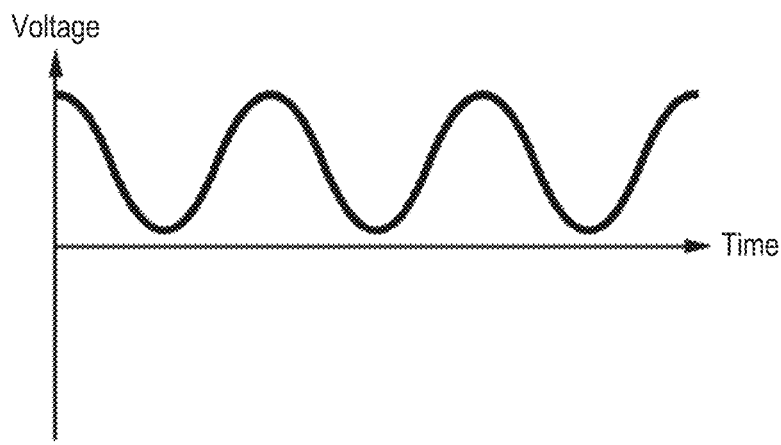
Figure 4C:
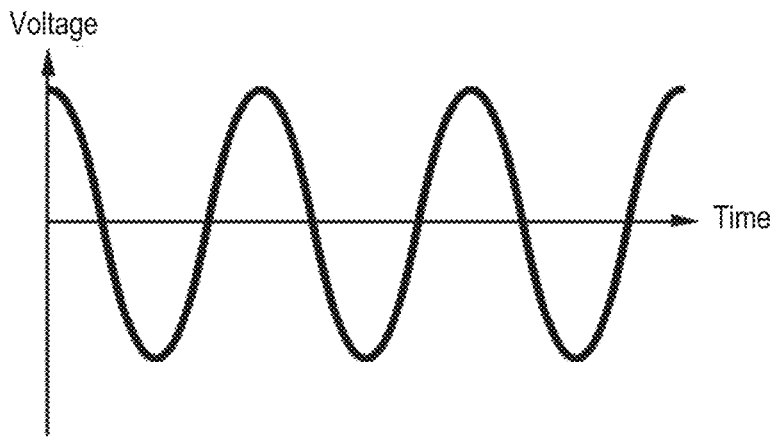

FIG. 3 is a block diagram illustrating the power unit 240 of the testing system 110 for measuring properties of particles in a fluid according to some embodiments of the present technology. FIGS. 4A, 4B, and 4C are diagrams illustrating various stages of the signal generated by the power unit 240 according to some embodiments of the present technology. Referring to FIGS. 3, 4A, 4B, and 4C together, the power unit 240 can include or couple to a power source 310, a function generator 320, and a signal converting unit 330. In some embodiments, the power source 310 (e.g., a battery) can provide a DC voltage, as illustrated in FIG. 4A.

The function generator 320 can be configured to generate an oscillating signal, such as by converting the DC voltage into an AC or a sinusoidal signal, as illustrated in FIG. 4B. The function generator 320 can generate the oscillating signals that have a continuous waveform with a predetermined period (e.g., a periodic signal). As such, the generated signals may be more suitable for detecting changes in electrical characteristics (e.g., phase change, amplitude change) caused by particles. The function generator 320 may be implemented in various forms, such as a micro control unit, an inverter, a converter, a pulse width modulator, a switch, a logic, a set of one or more passive components, etc.

The signal converting unit 330 can then amplify and adjust the oscillating signal by a predetermined offset, as illustrated in FIG. 4C. The signal converting unit 330 can generate a reference signal by converting, amplifying, and offsetting the oscillating signal such that the resulting reference signal is centered at 0V with repeating positive and negative voltage values (e.g., a sinusoidal wave). The resulting reference signal can be provided as a processing input signal. The frequency can be set to a predetermined level (e.g., between 1 kHz and 100 kHz) that avoids electrolysis of the solution under analysis while reducing power consumption.

The testing system 110 can be configured to communicate the generated reference signal through the electrodes on the fluid sample chip 230, across the detection regions, and then to the measurement unit 210 (e.g., the sensor circuit therein). As described above, the communicated reference signal can correspond to a reference state when the particulates are note located at the detection regions. In comparison, the reference signal can be altered by the particulates when or as they reach and pass through the detection regions. The measurement unit 210 can detect and process the changes in the communicated signal to determine and measure various aspects of the fluid and/or the particulates.

In some embodiments, the fluid sample chip 230 can include a set of three electrodes that form two adjacent and overlapping pairings of electrodes (a first electrode and a second electrode are coupled to the microchannel on opposite sides of a common electrode) on a substrate. Each pairing of the electrodes can provide parallel paths for the input reference signal. As the particulate passes between the first pairing of electrodes, the signal communicated across the corresponding path can change while the signal passing through the second pairing of electrodes remains at the reference state. The signal communicated through the first paring can return to the reference state and the signal communicated through the second pairing can experience the change as the particulate exits out of the first pairing and travels through between the second pairing. The measurement unit 210 can be configured to receive and compare, such as by observing the difference between, the reference signal communicated through the parallel paths.

Figure 5:
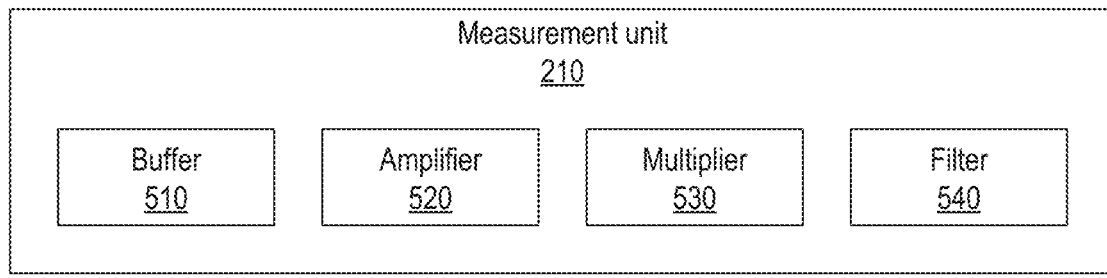
FIG. 5 is a block diagram illustrating a measurement unit of the testing system according to some embodiments of the present technology.

FIG. 5 is a block diagram illustrating the measurement unit 210 of the testing system 110 according to some embodiments of the present technology. FIGS. 6A, 6B, 6C, and 6D are diagrams illustrating various states of an output signal processed by the measurement unit 210 according to some embodiments of the present technology. Referring to FIGS. 5, 6A, 6B, 6C, and 6D together, the measurement unit 210 can include a buffer 510, an amplifier 520, a multiplier 530, and a filter 540.

Due to the electrical characteristics of the solution and the particles inside, an electrical signal output from the sensor (e.g., a signal communicated through one leg of the circuit bridge) may have complex characteristics, as illustrated in FIG. 6A. The measurement unit 210 can include one or more circuits and/or software modules configured to preprocess or filter the signal to address the complexities. The buffer 510 can be configured provide and utilize a nearly infinite input impedance in relaying the output signal from the sensor circuit to the amplifier 520 while minimizing undesired effects (e.g., noise) from components of another circuit of the measurement unit 210.

The amplifier 520 can be configured to calculate a difference between the reference signals communicated across the parallel legs and initially amplify the resulting difference value. Because the input signal is likely to have various noise from the fluid or solution, the amplifier 520 can first reduce the noise relative to the targeted signal component by amplifying the difference value and extracting an asymmetric signal value generated by the particles without other aspects of the signal. The extracted result (e.g., the signal illustrated in FIG. 6B) can be provided to the multiplier 530.

The multiplier 530 can further amplify the difference signal and extract a portion thereof corresponding to a change in an electrical component caused by the particles. The signal amplification and extraction can include multiplying the input signal (e.g., the offset-adjusted sinusoidal wave output by the power unit 240) with the difference signal. FIG. 6C illustrates an example of the amplified signal produced by the multiplier 530.

The measurement unit 210 can mix or combine the amplified output signal (e.g., the result of compensation by the buffer and processing of the multiplier 530) with a frequency component and a DC voltage that corresponds to the constant value representing the phase difference. Accordingly, the filter 540 can remove a frequency component and generating a signal, as illustrated in FIG. 6D. The resulting signal can be a processed output signal that represents a phase difference remaining after removing the targeted frequency component. Removing the frequency component from the output signal can convert the signal corresponding to the initial DC power. Accordingly, the measurement unit 210 can increase the clarity of the extracted signal change caused by the particles. The signal output from the filter 540 can be a waveform having a unique shape that corresponds to the transient moments when the particles instantaneously passes through the position between the electrodes. In other embodiments, the output signal can include a non-periodic or periodic pattern (e.g., waveform, sinusoidal, square, triangle, or similar shapes of voltage levels measured over time). The corresponding processed output signal can represent the passage of the particle in the microchannel between the electrodes.

In other embodiments, the measurement unit 210 can include other preprocessing filters (e.g., digital filters) to reduce the noise in the difference signal and improve the signal-to-noise ratio (SNR). The particle measurement system 100 can include a database of signal patterns (e.g., waveform, sinusoidal, square, triangle) that correspond to certain types of particles (e.g., significantly deformed particles, white blood cells, diseased cells, overlapping cells). The particle measurement system 100 can match the detected signal pattern to a pattern in the database and either categorize it as unwanted noise and remove it, or record the type of particle as a data point. Additionally or alternatively, the measurement unit 210 can be configured to perform a frequency analysis of the difference signal, such as by performing a real-time Fourier Transform (e.g., Fast Fourier Transform (FFT)) for a rolling window of the difference signal. As such, when the difference signal has a response characteristic corresponding to an expected frequency range, the measurement unit 210 can identify the particulate reaching and passing through the detection regions.

Figure 7:
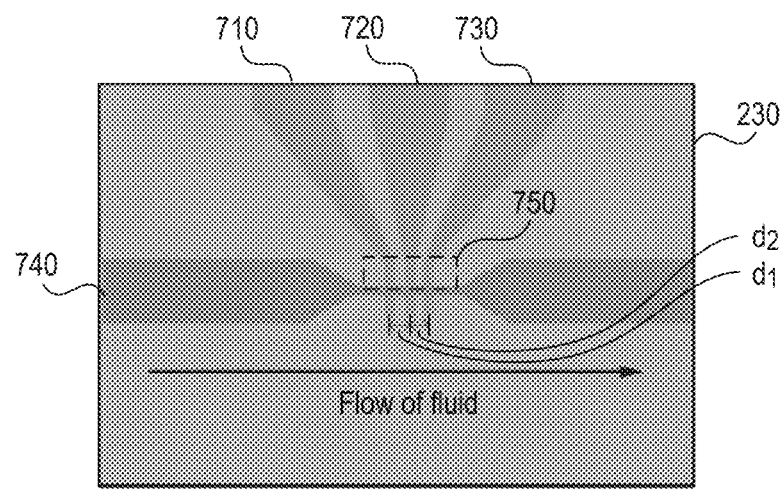
FIG. 7 is a diagram illustrating a fluid sample chip that can be used with the particle measurement system according to some embodiments of the present technology.

FIG. 7 is a diagram illustrating the fluid sample chip 230 that can be used with the particle measurement system 100 according to some embodiments of the present technology. The fluid sample chip 230 can include first, second, and third electrodes 710, 720, and 730. As discussed above (e.g., FIG. 2), the electrodes 710, 720, and 730 can be coupled to the circuit unit 220 and receive electrical communication of signals (e.g., the reference signal of FIG. 4C) from the power unit 240. In some embodiments, the second electrode 720 can receive the input/reference signal, while the first and third electrodes 710 and 730 send output signals to the circuit unit 220. In other embodiments, the electrode 720 can be grounded, and the first and third electrodes 710 and 730 can receive the input/reference signal that traversed through the sensors in the circuit unit 220.

The fluid sample chip 230 also includes a microchannel 740 configured to channel the fluid flowing and to which the electrodes 710, 720, and 730 are coupled at a microchannel-electrode coupling zone 750. The first and second electrodes 710 and 720 can form a first pair of electrodes and spaced apart by a first predetermined distance $d_1$. The location or the area between the first pair of electrodes can define a first detection region. Similarly, the second and third electrodes 720 and 730 can form a second pair of electrodes and spaced apart by a second predetermined distance $d_2$. The location or the area between the second pair of electrodes can define a second detection region. The testing system 110 can use the predetermined distances $d_1$ and $d_2$, as well as the measured wavelength of the difference signal, to calculate the microchannel passage speed and/or a size of a given particle in the microchannel.

The electrodes in the microchannel-electrode coupling zone 750 or otherwise proximate to the microchannel can extend perpendicular (i.e., orthogonal) to the microchannel to achieve more accurate signal readings. The separation distance between each pairing of electrodes 710, 720, and 730 can be based on an average and/or estimated length of the particulate (e.g., a red blood cell). In some embodiments, the separation distance can range between 5 and 25 micrometers. The length of each electrode can range between 5 and 25 micrometers. The width of each of the electrodes can increase at portions distant from the microchannel 740. In other words, the electrodes can limit the narrow width to portions closest to the microchannel, such as to facilitate the measurements, and have wider portions elsewhere to increase connection strength to other electrical components and to reduce heat generated by the signals passing through the electrodes.

Figure 8:
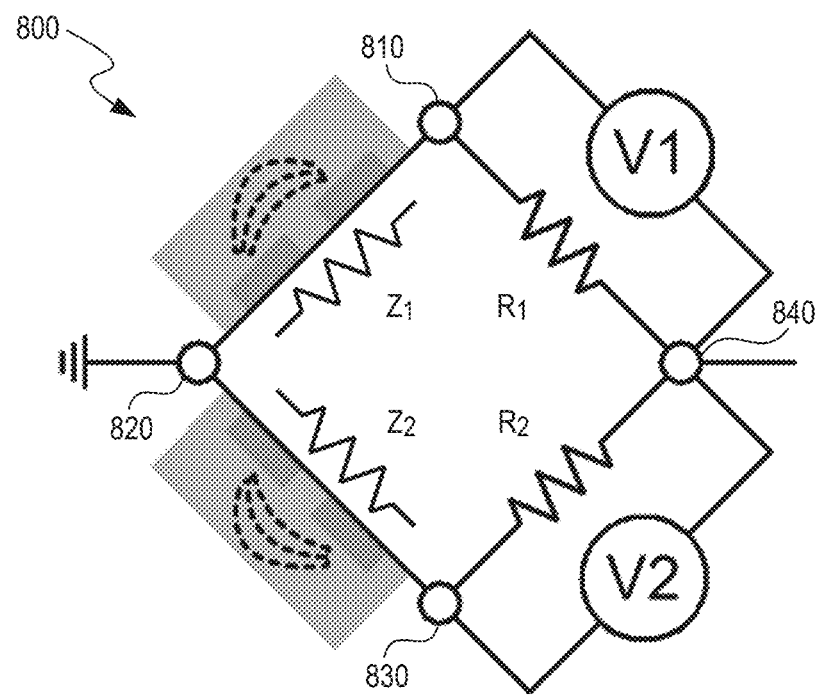
FIG. 8 is a diagram illustrating a sensor circuit used by the measurement unit according to some embodiments of the present technology.

FIG. 8 is a diagram illustrating a sensor circuit 800 used by the measurement unit 210 according to some embodiments of the present technology. In some embodiments, the sensor circuit 800 can be a Wheatstone bridge circuit, as illustrated. The sensor circuit 800 can include first, second, third, and fourth nodes 810, 820, 830, and 840. Each of the first three nodes 810, 820, and 830 can be coupled to each of the three electrodes 710, 720, and 730 illustrated in FIG. 7, respectively. As an illustrative example, the sensor circuit 800 can be formed when the fluid sample chip 230 is connected to the control apparatus of the testing system 110, such as when the electrodes 710, 720, and 730 are electrically coupled to the circuit unit 220 and/or the measurement unit 210. The sensor of the circuit unit 220 can include the node 840 configured to receive the reference signal. The sensor can include matching resistors connected parallel to the node 840 and voltage sensors measuring the voltage drop across the matching resistors. Connection points opposite the matching resistors can correspond to nodes 810 and 830, which may be electrically connected to the electrodes 710 and 730, respectively. Accordingly, the first and second detection regions (e.g., the portions of the microchannel 740 extending between the electrodes) can connect to the matching resistors and complete the parallels legs of the bridge circuit.

The top leg of the resulting sensor circuit 800 can include the impedance value (e.g., corresponding to the impedance of the electrolyte in the reference state and the combination of the electrolyte and the particulate in the altered state) across the first detection region $Z_1$ connected in series with a first resistor with a predetermined resistance value $R_1$. The bottom leg of the sensor circuit 800 can include the impedance value across the second detection region $Z_2$ connected in series with a second resistor with a predetermined resistance value $R_2$. The top and bottom legs of the Wheatstone bridge circuit can be connected in parallel. The measurement unit 210 can measure a first measured voltage value $V_1$ across the first resistor and a second measured voltage value $V_2$ across the second resistor. The Wheatstone bridge circuit can be balanced to an equilibrium state as represented by the equation:

$$Z_1 \times R_2 = Z_2 \times R_1.$$

As will be shown in FIGS. 9A-12B, as a particle moves through the microchannel across the different electrodes, the first and second impedance values change, thereby affecting the first and second measured voltage values $V_1$ and $V_2$.

Example Measurements and Analysis

Figure 9A:
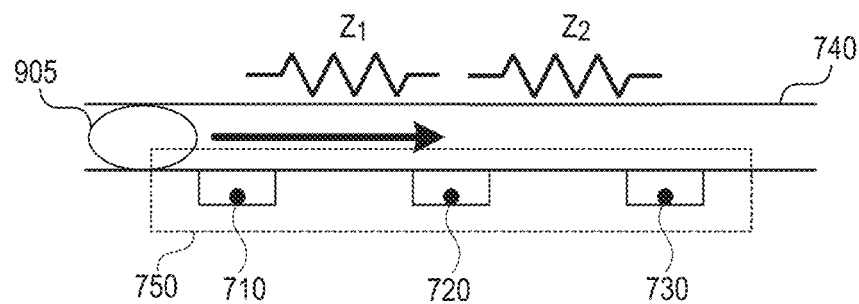
FIGS. 9A, 9B, and 9C are diagrams illustrating a red blood cell prior to entering a first detection region between a first pair of electrodes and the corresponding processed output signal according to some embodiments of the present technology.
Figure 9B:
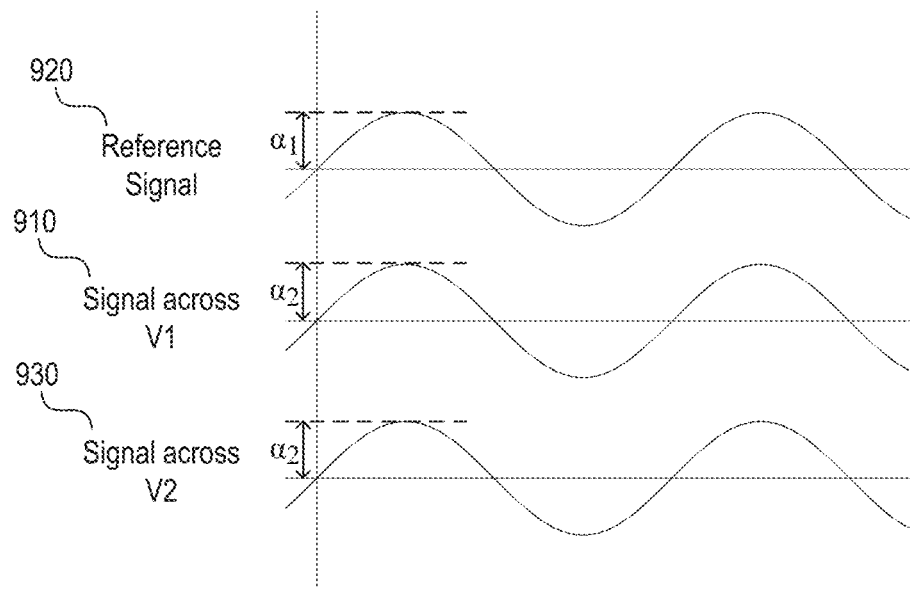
Figure 9C:
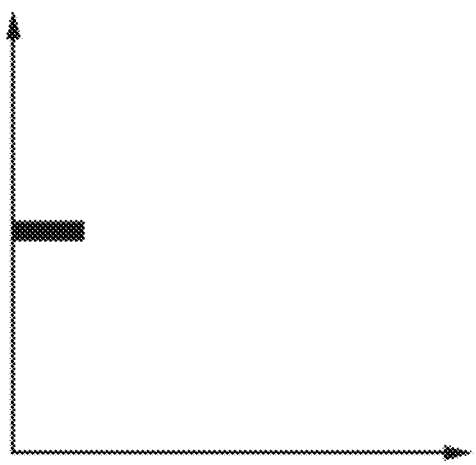

FIG. 9A is a diagram illustrating a particle 905 (e.g., red blood cell) prior to entering the first and second detection regions between the electrodes 710, 720, and 730 according to some embodiments of the present technology. In other words, FIG. 9A can represent the reference state with the electrolyte connecting both pairs of electrodes. The fluid in the first and second detection regions have equal impedance values (e.g., $Z_1=Z_2$). Accordingly, the first and second measured voltage values $V_1$ and $V_2$ can be equal and synchronized (e.g., having matching phases) with each other and/or the input electric signal. As illustrated in FIG. 9B, the reference signal (e.g., input signal applied to the second electrode 720) can have an amplitude $\alpha_1$ and the signals read across $V_1$ and $V_2$ in FIG. 8 can have an amplitude $\alpha_2$ (e.g., $\alpha_2<\alpha_1$ due to some resistance provided by the electrolyte). Given the matching conditions (e.g., $Z_1=Z_2$), the signals communicated through the first and second detection regions can match (e.g., no significant phase difference between the signals) because the particle 905 has not yet entered the detection regions. Therefore, the resulting difference between output signals from the filter 540, as illustrated in FIG. 9C without the noise component, can have a consistent and/or flat shape, similar to a DC voltage level. In some embodiments, the difference value can have a zero magnitude. In other embodiments, the difference value can be a non-zero value, such as due to slight mismatches in the electrode separation distances.

Figure 10A:
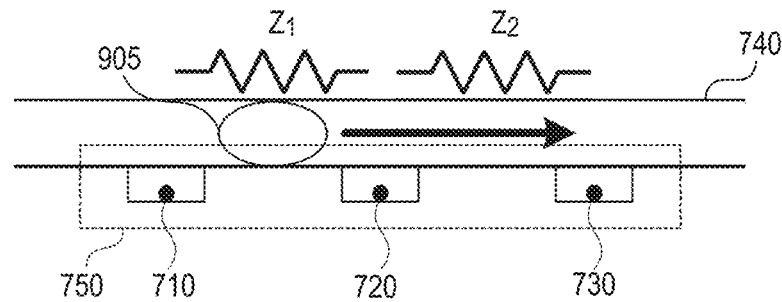
FIGS. 10A, 10B, and 10C are diagrams illustrating the red blood cell in the first detection region between the first pair of electrodes and the corresponding processed output signal according to some embodiments of the present technology.
Figure 10B:
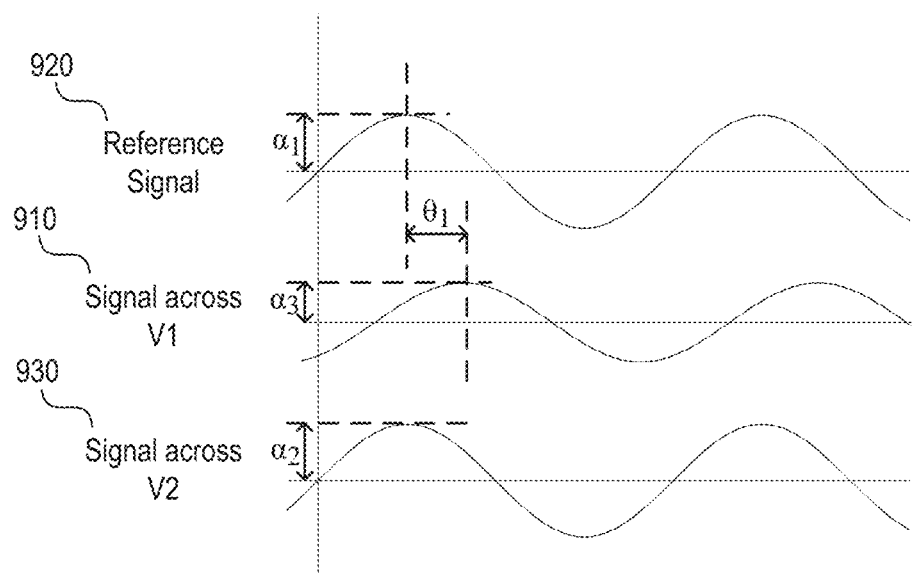
Figure 10C:
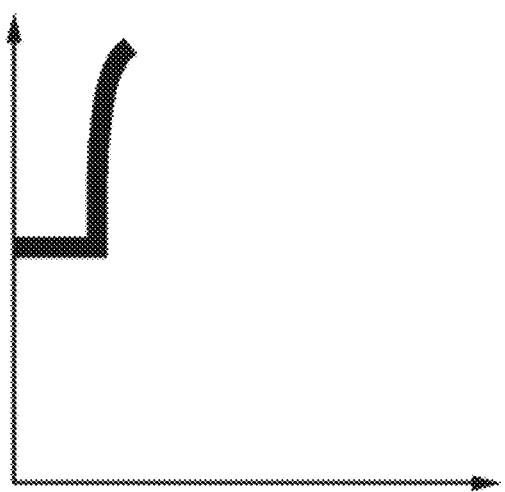

FIG. 10A is a diagram illustrating the particle 905 reaching the first detection region between the first pair of electrodes 710 and 720 according to some embodiments of the present technology. The particle can effectively act as a resistor and/or a capacitor between the first and second electrodes 710 and 720. As such, the particle at the first detection region can increase the first impedance value $Z_1$ and reduce the first measured voltage value $V_1$. As illustrated in FIG. 10B, the reference signal can have the amplitude $\alpha_1$, the signal read across $V_1$ can have an amplitude as, and the signal read across $V_2$ can have an amplitude $\alpha_2$ (e.g., $\alpha_3<\alpha_2$ due to the particle 905 increasing a voltage drop across the first detection region). Similarly, the particle at the first detection region can alter or shift a phase $\theta_1$ of the first measured voltage value $V_1$ while a phase $\theta_2$ (not shown in FIG. 10B) of the second measured voltage value $V_2$ remains constant (e.g., matching the reference signal). Accordingly, the processed/difference signal produced by the filter 540 can change and reflect the phase change and the difference between $V_1$ and $V_2$, as illustrated in FIG. 10C without the noise component. Alternatively, the filter 540 can be configured to detect the phase change by removing from the altered signal (e.g., $V_1$ measured over time) the reference signal and/or a signal having a frequency substantially similar to that of the input signal.

Figure 11A:
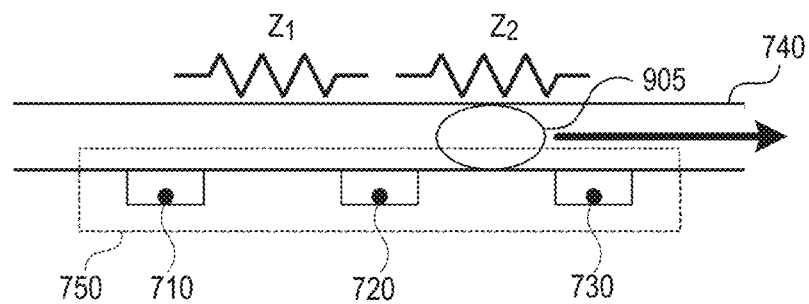
FIGS. 11A and 11B are diagrams illustrating the red blood cell in the second detection region between a second pair of electrodes and the corresponding processed output signal according to some embodiments of the present technology.
Figure 11B:
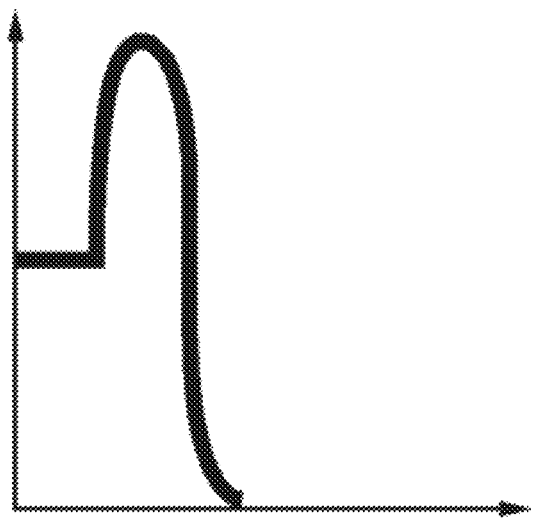

FIG. 11A is a diagram illustrating the particle 905 reaching the second detection region between the second pair of electrodes 720 and 730 (e.g., exiting the first detection region) according to some embodiments of the present technology. Again, the particle can effectively act as a resistor or a capacitor, thereby increasing the second impedance value $Z_2$ and reducing the first measured voltage value $V_2$. Similarly, the particle at the first detection region can alter a phase $\theta_2$ of the second measured voltage value $V_2$ while a phase $\theta_1$ of the first measured voltage value $V_1$ synchronizes with the reference signal. The signals read across $V_1$ and $V_2$ would look similar to those in FIG. 10B, but with the readout signals across $V_1$ and $V_2$ switched. Accordingly, the processed signal (e.g., the difference signal) produced by the filter 540 can change and reflect the phase change and the difference between $V_1$ and $V_2$, as illustrated in FIG. 11B without the noise component. Alter-natively, the filter 540 can be configured to detect the phase change by removing from the altered signal (e.g., $V_2$ measured over time) the reference signal and/or a signal having a frequency substantially similar to that of the input signal.

Figure 12A:
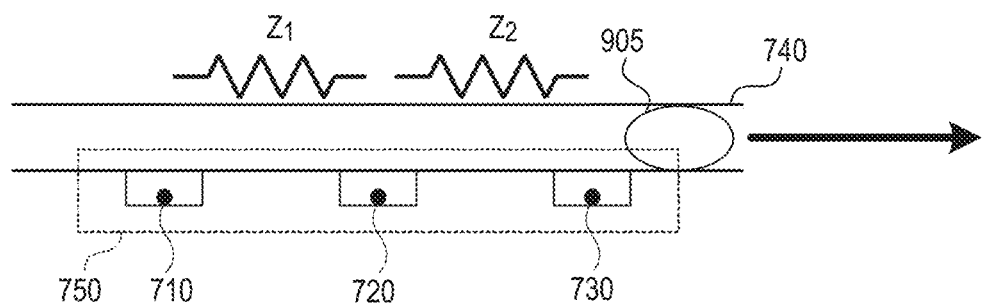
FIGS. 12A and 12B are diagrams illustrating the red blood cell after leaving the second detection region between the second pair of electrodes and the corresponding processed output signal according to some embodiments of the present technology.

FIG. 12A is a diagram illustrating the particle 905 exiting the second detection region between the second pair of electrodes 720 and 730 according to some embodiments of the present technology. In other words, FIG. 12A can illustrate the moment(s) after the particle travels past the electrode 730. As in FIGS. 9A and 9B, the effect/influence of the particle may be removed from the first or second impedance values $Z_1$ and $Z_2$. As a result the signal mirrored and communicating through the parallel legs of the sensor/bridge circuit can match each other with no phase difference between the signals. The voltage values $V_1$ and $V_2$ likewise can return to their original/reference state.

In some embodiments, the particles 905 can include cells (e.g., red blood cells). When a cell is positioned between adjacent electrodes, one or more properties of the cells can effectively cause the cell to function as a capacitor. Various properties of the cell (e.g., size, glycated hemoglobin level) may affect its resistance or capacitance value. In other words, one or more properties of the cell may be determined based on the processed signal.

Figure 12B:
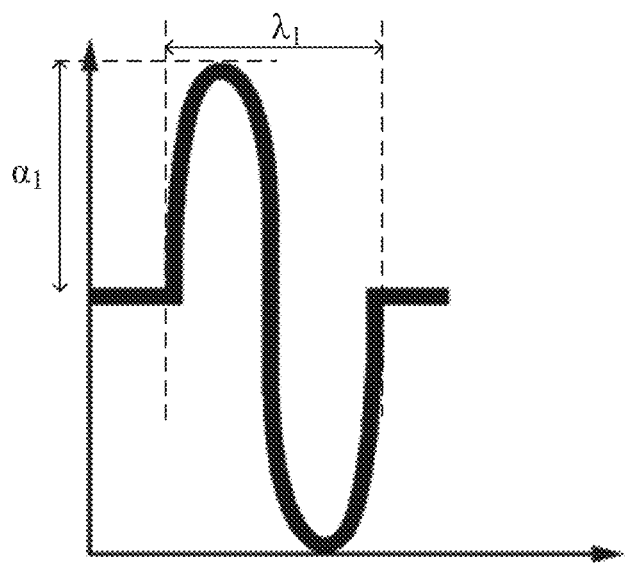

For example, the testing system 110 can count the number of particles by detecting the disruptions in the difference signal. Referring to FIG. 12B, the testing system 110 can also calculate the size of the particles using the amplitude $\alpha_1$ of the processed signal. The testing system 110 can also calculate the detection region passage time using the wavelength $\lambda_1$ of the processed signal. The testing system 110 can also calculate the elasticity of the particle 905 based at least on the detection region passage time, the dimensions of the microchannel, and a reference elasticity. The microchannel 740 can alter the configuration of the particles (e.g., by compressing or deforming the red blood cells) to affect movement of the particles along the microchannel 740 due to, for example, interaction between surfaces of the microchannel 740 and the particle. For example, frictional forces between surfaces of the microchannel 740 and the particle 905 can be proportional to the outward pressure applied by compressed particles to the walls of the microchannel 740. The microchannel 740 can be configured to transport or convey (i.e., allow sliding of) the compressed particles along the microchannel 740. The flow rate or speed of the compressed particles can depend on at least the pushing force (e.g., pump), capillary forces, and/or frictional forces between the particles and the inner walls of the microchannel 740. The frictional forces are greater for stiffer particles (e.g., red blood cells associated with higher A1c hemoglobin levels), thereby causing those stiffer particles to travel at a lower speed than highly compliant particles (e.g., red blood cells associated with lower A1c hemoglobin levels). This results in movement of the particles along microchannel 740 indicating one or more characteristics (e.g., A1c hemoglobin levels). The configuration of the microchannel 740 can be selected based on the characteristic(s) of the particles to be analyzed and detection techniques (e.g., impedance detection techniques, optical detection techniques, etc.).

In some embodiments, the microchannel 740 can have dimensions smaller than the particle 905 when uncompressed such that the microchannel compresses and reduces the dimensions of the particle. For example, the average human red blood cell can have a diameter around 7 to 8 micrometers and a thickness around 2-3 micrometers. Accordingly, the width of the microchannel 110 can range between 4 and 10 micrometers, and the height of the microchannel 110 can range between 1 and 5 micrometers. The compression can be used to measure other properties, such as a changed elasticity of the particle (e.g., cell) reflecting exposure to or influences from various substances (e.g., blood glucose) and/or aging. Such influences can affect the rigidity, stiffness, compliance, elastic modulus, and/or deformability of the cells, such as by hardening the cells and decreasing their elasticity.

Given the compression and increased rigidity, the time required for the particle 905 to pass through the microchannel 740 may be increased. Accordingly, the testing system 110 can identify characteristics of the cells according to a predetermined (e.g., proportionality) relationship between the passage time (e.g., the wavelength of the output signal) and factors affecting cell rigidity. As a result, the testing system 110 can provide data that characterizes biological conditions (e.g., a diagnosis of a disease, such as diabetes, or an assessment for a treatment) of a patient providing the cells.

For example, a red blood cell can have increased stiffness due to glycated hemoglobin. The stiffer red blood cells can require a longer time to pass through the microchannel compared to more flexible red blood cells. The testing system 110 can measure the degree of glycation of an individual red blood cell according to a proportional relationship between the passage time and a glycated hemoglobin level (HbA1C level).

Figure 13:
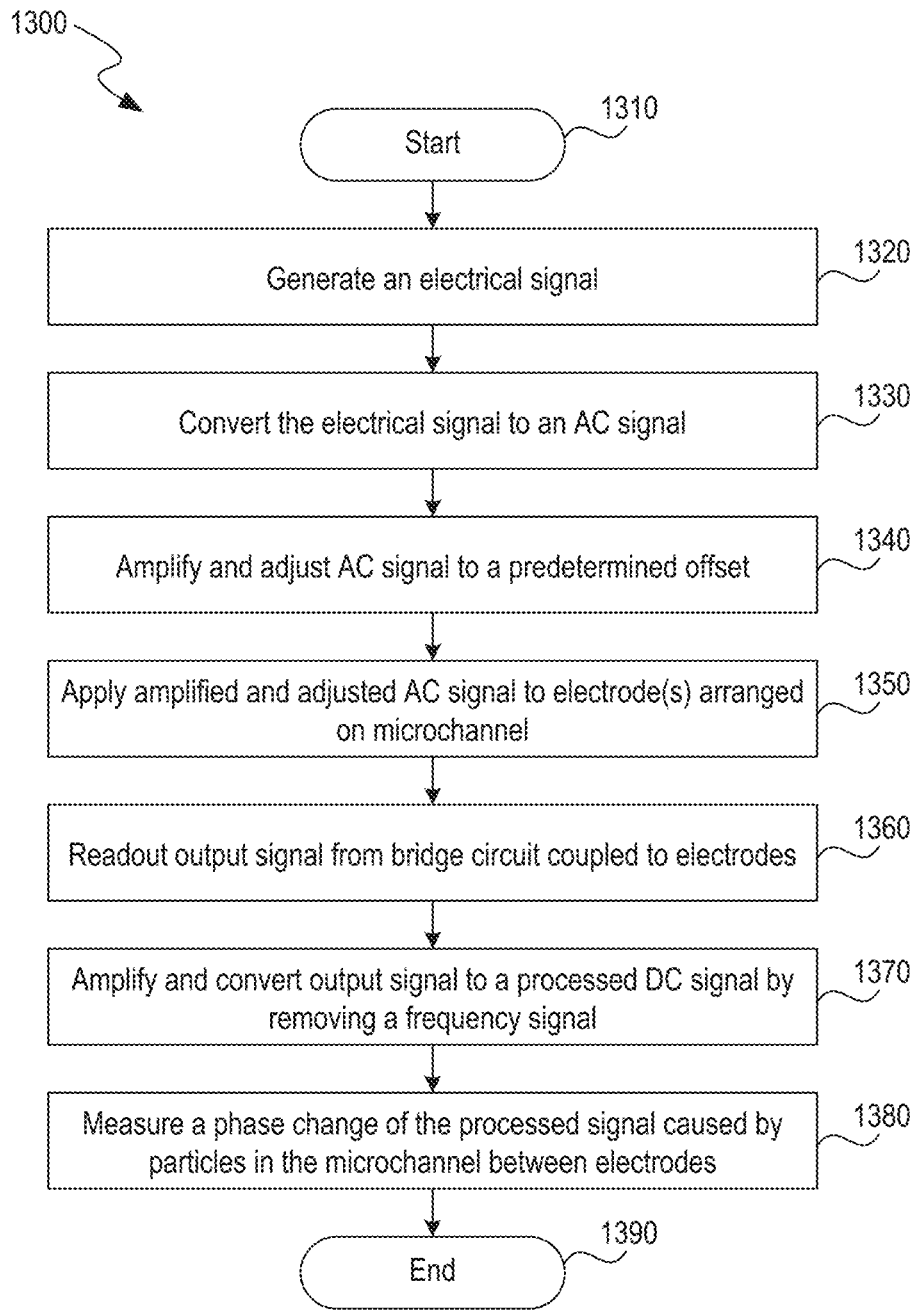
FIG. 13 is a flow diagram illustrating a method 1300 of measuring properties of particles in a fluid according to some embodiments of the present technology.

FIG. 13 is a flow diagram illustrating a method 1300 of measuring properties of particles in a fluid according to some embodiments of the present technology. The method 1300 can be implemented by the particle measurement system 100 (via, e.g., the testing system 110).

At block 1320, the method 1300 can include generating an electrical signal. This can be done using, for example, the power source 310. Next, at block 1330, the method 1300 can include converting the electrical signal, such as from a DC voltage, to an oscillating signal. This can be done using, for example, the function generator 320. Next, a block 1340, the method 1300 can include amplifying and adjusting the AC signal to a predetermined offset. This can be done using, for example, the signal converting unit 330.

Next, at block 1350, the method 1300 can include applying the amplified and adjusted AC signal (e.g., the reference signal) to one or more electrodes arranged on a microchannel through which fluid with particles flows. Next, at block 1360, the method 1300 can include reading the output signal communicated through the electrodes. The electrodes may be coupled to or be part of, for example, the measurement unit 210 and the sensor circuit described above. Next, at block 1370, the measurement unit 210 can amplify and convert the output signal to a processed DC signal by removing a frequency signal. The removed frequency can be set to be the same as or similar to a frequency of the input signal. Next, at block 1380, the method 1300 can include measuring a phase change of the processed signal (e.g., the amplitude and/or a duration of a non-zero portion of the difference signal) attributable to the particles being present in the microchannel, and more specifically in the detection region(s) between the electrodes.

Figure 14:
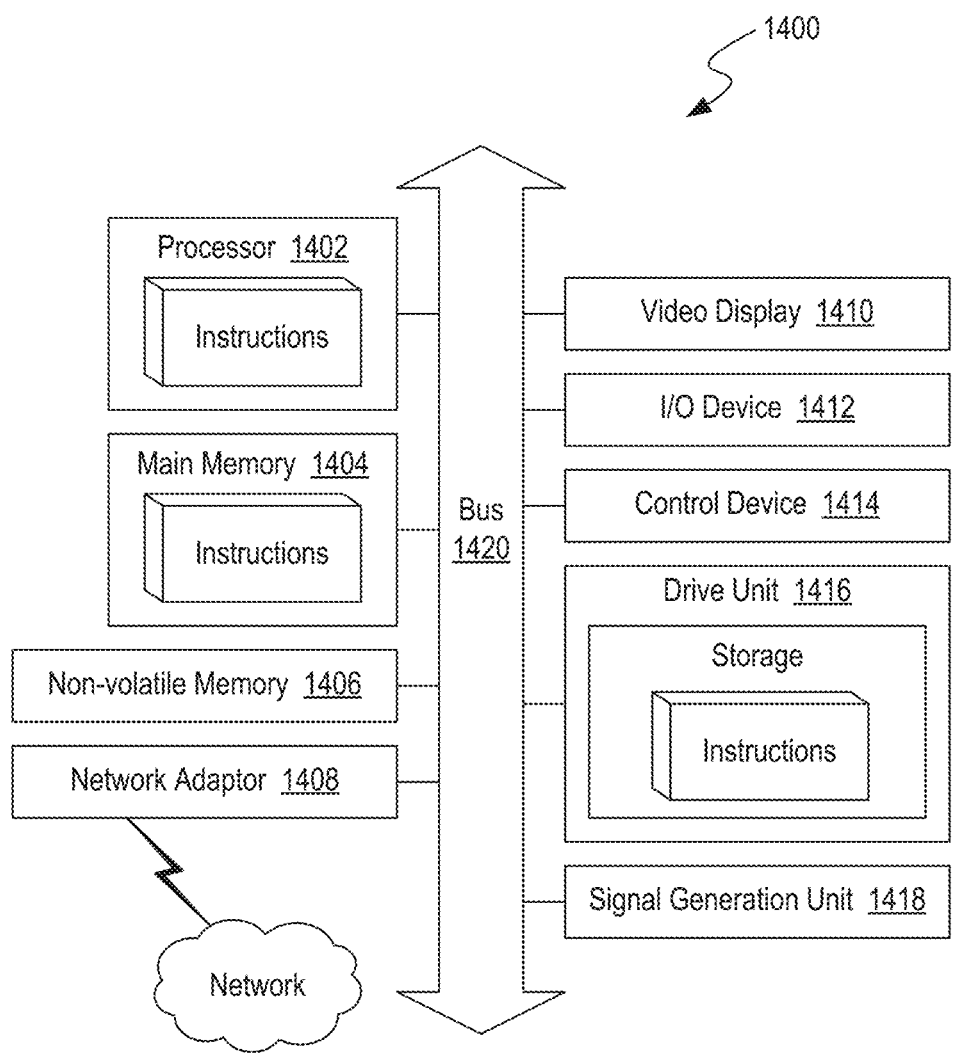
FIG. 14 is a block diagram illustrating an example of a processing system 1400 in which at least some operations described herein can be implemented.

FIG. 14 is a block diagram illustrating an example of a processing system 1400 in which at least some operations described herein can be implemented. For example, a computing device (e.g., the particle measurement system 100, the testing system 110, one or more of the client computing devices 120, one or more of the servers, or a combination thereof of FIG. 1) and/or the method 1300 of FIG. 13 can be implemented using the processing system 1400.

The processing system 1400 can include one or more central processing units 1402 ("processors"), main memory 1404, non-volatile memory 1406, network adapters 1408 (e.g., network interfaces), video displays 1410, input/output devices 1412, control devices 1414 (e.g., keyboard and pointing devices), drive units 1416 including a storage medium, and/or signal generation devices 1418 that are communicatively connected to a bus 1420. The bus 1420 is illustrated as an abstraction that represents one or more physical buses and/or point-to-point connections that are connected by appropriate bridges, adapters, or controllers. The bus 1420, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1400 can operate in the capacity of a server or a client machine in a client-server network environment, or as a peer machine in a peer-to-peer network environment. The processing system 1400 can be an analysis circuit within a medical device, a server, a personal computer, a tablet computer, a personal digital assistant (PDA), a mobile phone, a gaming console, a gaming device, a music player, a wearable electronic device, a network-connected ("smart") device, a virtual/augmented reality system, or any other machine capable of executing a set of instructions (sequential or otherwise) that specify actions to be taken by the processing system 1400.

While the main memory 1404, the non-volatile memory 1406, and the storage medium (also called a "machine-readable medium") are shown to be a single medium, the term "machine-readable medium" and "storage medium" should be taken to include a single medium or multiple media (e.g., a centralized or distributed database, and/or associated caches and servers) that store one or more sets of instructions. The term "machine-readable medium" and "storage medium" shall also be taken to include any medium that is capable of storing, encoding, or carrying a set of instructions for execution by the processing system 1400.

In general, the routines executed to implement the embodiments of the disclosure can be implemented as part of an operating system or a specific application, component, program, object, module, or sequence of instructions (collectively referred to as "computer programs"). The computer programs typically comprise one or more instructions (e.g., instructions) set at various times in various memory and storage devices in a computing device. When read and executed by the one or more processors, the instruction(s) cause the processing system to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices, floppy and other removable disks, hard disk drives, optical disks (e.g., Compact Disk Read- Only Memory (CD ROMS), Digital Versatile Disks (DVDs)), and transmission-type media such as digital and analog communication links.

The network adapter 1408 enables the processing system to mediate data in a network with an entity that is external to the processing system through any communication protocol supported by the processing system and the external entity. The network adapter 1408 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1408 can include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

As described above, in some embodiments, the degree of glycation can be measured using changes in the physical characteristics of red blood cells due to the glycation. In some embodiments, systems that use the disclosed technology (e.g., calculating the hardness of each individual red blood cell based on their microchannel passage time) can determine the degree of glycation more stably in response to external and human factors compared to equipment using biochemical techniques. In some embodiments, the particle measurement system can detect minute electrical changes that occur due to the passage of red blood cells using a circuit configuration and determine the degree of glycation of the red blood cells. In some embodiments, the particle measurement system can be used directly for clinical diagnosis by correcting an initial calculation of the glycated hemoglobin level using an individual user's reference value.

Furthermore, the particle measurement system can be implemented with a computer-readable storage medium or a similar device using, for example, software, hardware, or a combination thereof. In a hardware implementation, the particle measurement system can be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and electric units for performing other functions. In some embodiments, the particle measurement system can be implemented by a control module itself. In a software implementation, one or more aspects of the particle measurement system, such as the procedures and functions described above, can be implemented as separate software modules. Each of the software modules can perform one or more functions and operations described in the present specification. Software code can be implemented in software applications written in a suitable programming language. The software code can be stored in a memory module and can be executed by the control module.

The embodiments, features, systems, devices, materials, methods and techniques described herein may, in some embodiments, be similar to any one or more of the embodiments, features, systems, devices, materials, methods and techniques described in the following:

Korean Patent Application No. 10-2021-0128520, filed Sep. 29, 2021, issued as Korean Patent No. 10-2439474;

International Application PCT/KR2021/018280, filed Dec. 3, 2021;

U.S. Application titled APPARATUS FOR MEASURING GLYCATION OF RED BLOOD CELLS AND GLYCATED HEMOGLOBIN LEVEL USING PHYSICAL AND ELECTRICAL CHARACTERISTICS OF CELLS, AND RELATED METHODS, filed on Dec. 9, 2022; and listing inventors: Ung-Hyeon Ko; Seung-Jin Kang; and Eun-Young Park;

International Application PCT/KR2022/019905, filed Dec. 8, 2022; and

Korean Patent Application No. 10-2022-0031378, filed Mar. 14, 2022.

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The above description is merely illustrative of the technical idea of the present disclosure, and various modifications, changes, and substitutions can be made by those skilled in the art without departing from the essential features of the present disclosure. Accordingly, the embodiments described above and in the accompanying drawings are intended to describe the present technology without limiting the associated technical ideas. The scope of the present technology is not limited by any of the embodiments described above and the accompanying drawings.

It will be apparent to those having skill in the art that changes can be made to the details of the above-described embodiments without departing from the underlying principles of the present disclosure. In some cases, well known structures and functions have not been shown or described in detail to avoid unnecessarily obscuring the description of the embodiments of the present technology. Although steps of methods can be presented herein in a particular order, alternative embodiments can perform the steps in a different order. Similarly, certain aspects of the present technology disclosed in the context of particular embodiments can be combined or eliminated in other embodiments. Furthermore, while advantages associated with certain embodiments of the present technology can have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics can be combined in any suitable manner in one or more embodiments.

Unless indicated to the contrary, the numerical parameters set forth in the following specification and attached claims are approximations that can vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

We claim:

1. A method of analyzing red blood cells in a patient blood sample, the method comprising:
   transferring one or more red blood cells through a microchannel sized to compress the one or more red blood cells;
   analyzing, using one or more sensor circuits positioned along the microchannel, movement of individual ones of the one or more red blood cells moving along and compressed by the microchannel, wherein the movement is related to an analyte characteristic of the corresponding one or more red blood cells; and
   determining the analyte characteristic of the one or more red blood cells based on the analyzed movement of the one or more red blood cells, wherein the analyte characteristic indicates a glycated hemoglobin level of the one or more red blood cells.

2. The method of claim 1, wherein the microchannel is sized to compress the one or more red blood cells such that the movement of the one or more red blood cells is affected by a stiffness of the respective one or more red blood cells, and wherein the analyte characteristic is correlated with the stiffness of the respective one or more red blood cells.

3. The method of claim 1, wherein analyzing the movement of individual ones of the one or more red blood cells comprises determining:
   a first travel speed of the individual ones of the one or more red blood cells at a first region in the microchannel; and
   a second travel speed of the individual ones of the one or more red blood cells at a second region in the microchannel.

4. The method of claim 3, further comprising analyzing signals from the one or more sensor circuits to determine the first travel speed and the second travel speed for the individual ones of the one or more red blood cells, wherein the microchannel is configured to compress the individual one or more red blood cells such that the first travel speed is different from the second travel speed.

5. The method of claim 3, wherein analyzing the movement of individual ones of the one or more red blood cells is based on a combination of the first travel speed and the second travel speed for the individual ones of the one or more red blood cells.

6. The method of claim 1, wherein analyzing the movement of individual ones of the one or more red blood cells comprises determining an acceleration of the individual ones of the one or more red blood cells along at least a portion of the microchannel.

7. The method of claim 1, further comprising:
   determining at least one travel parameter for individual ones of the one or more red blood cells at multiple locations along the microchannel using the one or more sensor circuits, wherein the one or more sensor circuits are configured to take electrical measurements at the multiple locations, and wherein the analyte characteristic of the one or more red blood cells is determined based on the at least one travel parameter.

8. The method of claim 1, further comprising, for individual ones of the one or more red blood cells:
   communicating a first reference signal through the red blood cell at a first region in the microchannel; and
   communicating a second reference signal through the red blood cell at a second region in the microchannel,
   wherein analyzing the movement of red blood cell comprises:
      determining, using the one or more sensor circuits, a first phase change representing a phase change of the first reference signal induced by the red blood cell at the first region; and
      determining, using the one or more sensor circuits, a second phase change representing a phase change of the second reference signal induced by the red blood cell at the second region.

9. The method of claim 8, wherein:
   the first region includes a first detection region and a second detection region,
   the second region includes a third detection region and a fourth detection region,
   the first phase change is determined based on a difference between (1) a first signal comprising the first reference signal communicated across the first detection region and (2) a second signal comprising the first reference signal communicated across the second detection region; and
   the second phase change is determined based on a difference between (1) a third signal comprising the second reference signal communicated across the third detection region and (2) a fourth signal comprising the second reference signal communicated across the fourth detection region.

10. The method of claim 8, wherein:
the first phase change is determined based on a difference between (1) a first signal comprising the first reference signal communicated across at least a portion of the first region and (2) the first reference signal; and
the second phase change is determined based on a difference between (1) a second signal comprising the second reference signal communicated across at least a portion of the second region and (2) the second reference signal.

11. A computer-readable storage medium storing instructions that, when executed by one or more processors in an analyte characteristic measuring system, cause the system to perform operations comprising:
transferring one or more red blood cells through a microchannel sized to compress the one or more red blood cells;
analyzing, using one or more sensor circuits positioned along the microchannel, movement of individual ones of the one or more red blood cells moving along and compressed by the microchannel, wherein the movement is related to an analyte characteristic of the corresponding one or more red blood cells; and
determining the analyte characteristic of the one or more red blood cells based on the analyzed movement of the one or more red blood cells, wherein the analyte characteristic indicates a glycated hemoglobin level of the one or more red blood cells.

12. The computer-readable storage medium of claim 11, wherein the microchannel is sized to compress the one or more red blood cells such that the movement of the one or more red blood cells is affected by a stiffness of the respective one or more red blood cells, and wherein the analyte characteristic is correlated with the stiffness of the respective one or more red blood cells.

13. The computer-readable storage medium of claim 11, wherein analyzing the movement of individual ones of the one or more red blood cells comprises determining:
a first travel speed of the individual ones of the one or more red blood cells at a first region in the microchannel; and
a second travel speed of the individual ones of the one or more red blood cells at a second region in the microchannel.

14. The computer-readable storage medium of claim 13, wherein the operations further comprise analyzing signals from the one or more sensor circuits to determine the first travel speed and the second travel speed for the individual ones of the one or more red blood cells.

15. The computer-readable storage medium of claim 13, wherein analyzing the movement of individual ones of the one or more red blood cells is based on a combination of the first travel speed and the second travel speed for the individual ones of the one or more red blood cells.

16. The computer-readable storage medium of claim 11, wherein analyzing the movement of individual ones of the one or more red blood cells comprises determining an acceleration of the individual ones of the one or more red blood cells along at least a portion of the microchannel.

17. The computer-readable storage medium of claim 11, wherein the operations further comprise:
determining at least one travel parameter for individual ones of the one or more red blood cells at multiple locations along the microchannel using the one or more sensor circuits, wherein the one or more sensor circuits are configured to take electrical measurements at the multiple locations, and wherein the analyte characteristic of the one or more red blood cells is determined based on the at least one travel parameter.

18. The computer-readable storage medium of claim 11, wherein the operations further comprise, for individual ones of the one or more red blood cells:
communicating a first reference signal through the red blood cell at a first region in the microchannel; and
communicating a second reference signal through the red blood cell at a second region in the microchannel,
wherein analyzing the movement of red blood cell comprises:
determining, using the one or more sensor circuits, a first phase change representing a phase change of the first reference signal induced by the red blood cell at the first region; and
determining, using the one or more sensor circuits, a second phase change representing a phase change of the second reference signal induced by the red blood cell at the second region.

19. The computer-readable storage medium of claim 18, wherein:
the first region includes a first detection region and a second detection region,
the second region includes a third detection region and a fourth detection region,
the first phase change is determined based on a difference between (1) a first signal comprising the first reference signal communicated across the first detection region and (2) a second signal comprising the first reference signal communicated across the second detection region; and
the second phase change is determined based on a difference between (1) a third signal comprising the second reference signal communicated across the third detection region and (2) a fourth signal comprising the second reference signal communicated across the fourth detection region.

20. The computer-readable storage medium of claim 18, wherein:
the first phase change is determined based on a difference between (1) a first signal comprising the first reference signal communicated across at least a portion of the first region and (2) the first reference signal; and
the second phase change is determined based on a difference between (1) a second signal comprising the second reference signal communicated across at least a portion of the second region and (2) the second reference signal.

21. A system, comprising:
a fluid sample chip having a microchannel sized to compress one or more red blood cells moving along the microchannel; and
a controller programmed to perform a process including:
analyzing, using one or more sensor circuits positioned along the microchannel, movement of individual ones of the one or more red blood cells moving along and compressed by the microchannel, wherein the movement is related to an analyte characteristic of the corresponding one or more red blood cells; and
determining the analyte characteristic of the one or more red blood cells based on the analyzed movement of the one or more red blood cells, wherein the analyte characteristic indicates a glycated hemoglobin level of the one or more red blood cells.

22. The system of claim 21, wherein the microchannel is sized to compress the one or more red blood cells such that the movement of the one or more red blood cells is affected by a stiffness of the respective one or more red blood cells, and wherein the analyte characteristic is correlated with the stiffness of the respective one or more red blood cells.

23. The system of claim 21, wherein analyzing the movement of individual ones of the one or more red blood cells comprises determining:
- a first travel speed of the individual ones of the one or more red blood cells at a first region in the microchannel; and
- a second travel speed of the individual ones of the one or more red blood cells at a second region in the microchannel.

24. The system of claim 21, wherein the process further comprises:
- determining at least one travel parameter for individual ones of the one or more red blood cells at multiple locations along the microchannel using the one or more sensor circuits, wherein the one or more sensor circuits are configured to take electrical measurements at the multiple locations, and wherein the analyte characteristic of the one or more red blood cells is determined based on the at least one travel parameter.

* * * * *